US00PP08975P

United States Patent [19]

Brown

[11] Patent Number: Plant 8,975

[45] Date of Patent: Nov. 8, 1994

[54] AGLAONEMA PLANT NAMED RHAPSODY IN GREEN

[75] Inventor: B. Frank Brown, Palm Bay, Fla.

[73] Assignee: Sunshine Foliage World, Zolfo Springs, Fla.

[21] Appl. No.: 172,893

[22] Filed: Dec. 27, 1993

[51] Int. Cl.[5] ..... A01H 5/00
[52] U.S. Cl. ..... Plt./88.1
[58] Field of Search ..... Plt. 88.1

*Primary Examiner*—James R. Feyrer
*Attorney, Agent, or Firm*—Foley & Lardner

[57] ABSTRACT

An Aglaonama plant named Rhapsody in Green characterized by its bicolor leaves having a greyish green center with an irregular outer edge and a surrounding solid green area to the margin, long and narrow leaves, rapid growth habit with frequent suckering, roots rapidly, long and narrow spadix, and its ability to withstand temperatures as low as 38° F. with no damage.

1 Drawing Sheet

The present invention comprises a new and distinct cultivar of Aglaonema, botanically known as *Aglaonema nitidum,* and referred to by the cultivar name Rhapsody in Green.

The new cultivar is a product of a planned breeding program carried out by inventor B. Frank Brown in Valkaria, Fla. The seed parent was an unnamed *Aglaonema nitidum* cultivar characterized by gray stripes on a dark green leaf. The pollen parent was Ernesto's Favorite, an *Aglaonema nitidum* cultivar primarily characterized by a relatively wide (5 to 8 cm) silver band covering the center of the leaf blade, surrounded by a light green border.

The new cultivar was discovered and selected from the progeny of the stated cross by B. Frank Brown in Valkaria, Fla. Asexual propagation by division carried out by B. Frank Brown in Valkaria, Fla., and later carried out in Zolfo Springs, Fla., was used to increase the number of plants for evaluation and has demonstrated the stability of the characteristics of the new cultivar from generation to generation.

The following observations, measurements and values describe plants of the new cultivar grown in Valkaria, Fla. under shadehouse conditions which closely approximate those generally used in horticultural practice.

The following traits have been repeatedly observed to be characteristics which in combination distinguish the new cultivar from other Aglaonema of the same general type.

1. Bicolored leaves comprising a greyish green center with an irregular outer edge, and a surrounding solid green area to the margin.
2. The leaves are relatively long and narrow.
3. Growth is more rapid than for other cultivars, and it suckers more frequently.
4. Roots more rapidly than known cultivars,
5. Very cold hardy, withstanding temperatures as low as 38° F. with no damage.
6. Petioles tend to elongate on plants grown in low light.
7. Floral characteristics are unlike the flowers of either parent, with the spadix of the new cultivar being both longer and narrower.
8. Petioles tend to be generally equal in length to the length of the leaf blade.

When compared to its pollen parent, Rhapsody in Green has smaller leaves with more contrasting color, a more rapid growth habit, higher branching capability, roots more quickly, and is more compact in appearance. The new cultivar is distinguished from its seed parent primarily by its more frequent suckering, smaller leaves, and its light green center bordered by dark green. In general comparison to other Aglaonema cultivars of this general type, Rhapsody in Green suckers more frequently, roots more quickly and has a more rapid growth habit.

All color references are to the Royal Horticultural Society Colour Chart. Colors may vary somewhat depending on horticultural practices such as light level and fertilization rate, among others, without, however any variance in genotype.

The color photographic drawing comprises a top perspective view of Rhapsody in Green.

The photograph is of an unpruned plant of the new cultivar twenty-one (21) months in age, grown under appropriate growing conditions. The vigor, compactness and frequency of suckering of the new cultivar will be apparent from the photograph. Colors are as accurate as possible with color illustrations of this type.

Classification: *Aglaonema nitidum,* cv, Rhapsody in Green.

Propagation: Asexual propagation either by division or tissue culture.

Plant: When a 10 leaf cutting is grown in a 10 cm pot for approximately 20–30 weeks under appropriate growing conditions, Rhapsody in Green is approximately 11.0 cm to 17.0 cm in height, measured from the soil surface to the junction of the petioles of the last two (2) unrolled leaves, and approximately 24 cm to 30 cm in width. When fully mature, the new cultivar will reach 90–100 cm in both height and width.

Stem:

*Growth pattern.*—The stem is erect in growth and is approximately 1.5 cm to 2.0 cm in diameter 1 cm above the soil surface.

*Color.*—The stem color is closest to 137A.

Petiole:

*Growth pattern.*—The petiole has fleshy edges, referred to as wings, extending from the midrib. The wings are approximately 3 mm to 4 mm wide one-half the distance from the petiole base to the wing apex. The wings extend from the base of the petiole to within approximately 5.0 cm to 6.0 cm of the base of the leaf.

*Dimensions.*—The petiole is straight from its base to approximately the end of the wing, and often curved from approximately the end of the wing to the base of the leaf. The petiole is approximately 5 mm in diameter one-half the distance between the top of the wing and the base of the leaf. The petiole is approximately 16.0 cm to 20.0 cm in length.

*Color.*—The petiole is 137 B-C, with the petiole wings being somewhat darker, approximately 137 A-B.

Leaf:

*Growth pattern.*—The leaf is long and narrow with an acuminate apex and an acute base. The margin is entire. The leaf is asymmetric with the side of the leaf unrolling first having less surface area than the side unrolling last. The leaf is oriented parallel to the stem axis at the time of full unrolling, changing to approximately 40 degrees above perpendicular to the stem axis as more leaves unroll above it. The leaf blade is flat from the midrib to the margin, and somewhat wavy along the margin.

*Dimensions.*—For the pot size and growing time indicated, average mature leaves are approximately 26 to 42 cm long and approximately 5 to 11 cm wide.

*Midrib.*—The midrib is thick and prominent, recessed on the adaxial or upper leaf surface and protruding from the abaxial or lower surface. The color of the adaxial leaf midrib is indistinguishable from the surrounding leaf center color (noted below) for both new and mature leaves. The abaxial or underside leaf midrib is closest to 146 C-D on both new and old leaves.

*Primary veins.*—The primary veins are sunken into the upper surface and protrude slightly from the underside. The primary veins are indistinguishable in color from the color of the surrounding leaf surface.

*Color and pattern.*—The leaf is bicolor on the adaxial or upper surface, with a greyish green center extending from the midrib to an irregular edge pattern approximately 1 cm to 3 cm from leaf margins. The area from the irregular edge to the margin is light to medium green depending on age of leaf. The center color of new leaves is 191B, with the surrounding green areas being 137C. Older leaves have a center color closest to 194A, with the green surrounding area being between 137A and 139A. The under surface of both new and old leaves is solid, approximately 137C.

*Axillary breaks.*—There are numerous axillary breaks off the main stem, with at least one leaf expanded. The axillary stems are similar in color to the main stem.

*Inflorescence.*—Spathe is approximately 7.5 cm in length and 3.5 cm in width, and is approximately 191B in color. The spadix is relatively long (4 cm) and narrow (7 mm in diameter) and white in color. There are approximately 5-10 pistillate female flowers.

*Roots.*—Relatively long and narrow roots with fine laterals; dark cream in color.

General observations: Rhapsody in Green has long and narrow bicolor leaves comprised of a greyish green irregular shaped center region and solid green near the leaf margins. The plant habit is strongly branched and dense. The plant grows very rapidly, attaining a marketable size in less time than present commercial cultivars. The plant is cold hardy, withstanding temperatures as low as 38° F. with no damage. These combined characteristics make Rhapsody in Green a unique new cultivar.

I claim:

1. A new and distinct cultivar of Aglaonema plant named Rhapsody in Green, as illustrated and described.

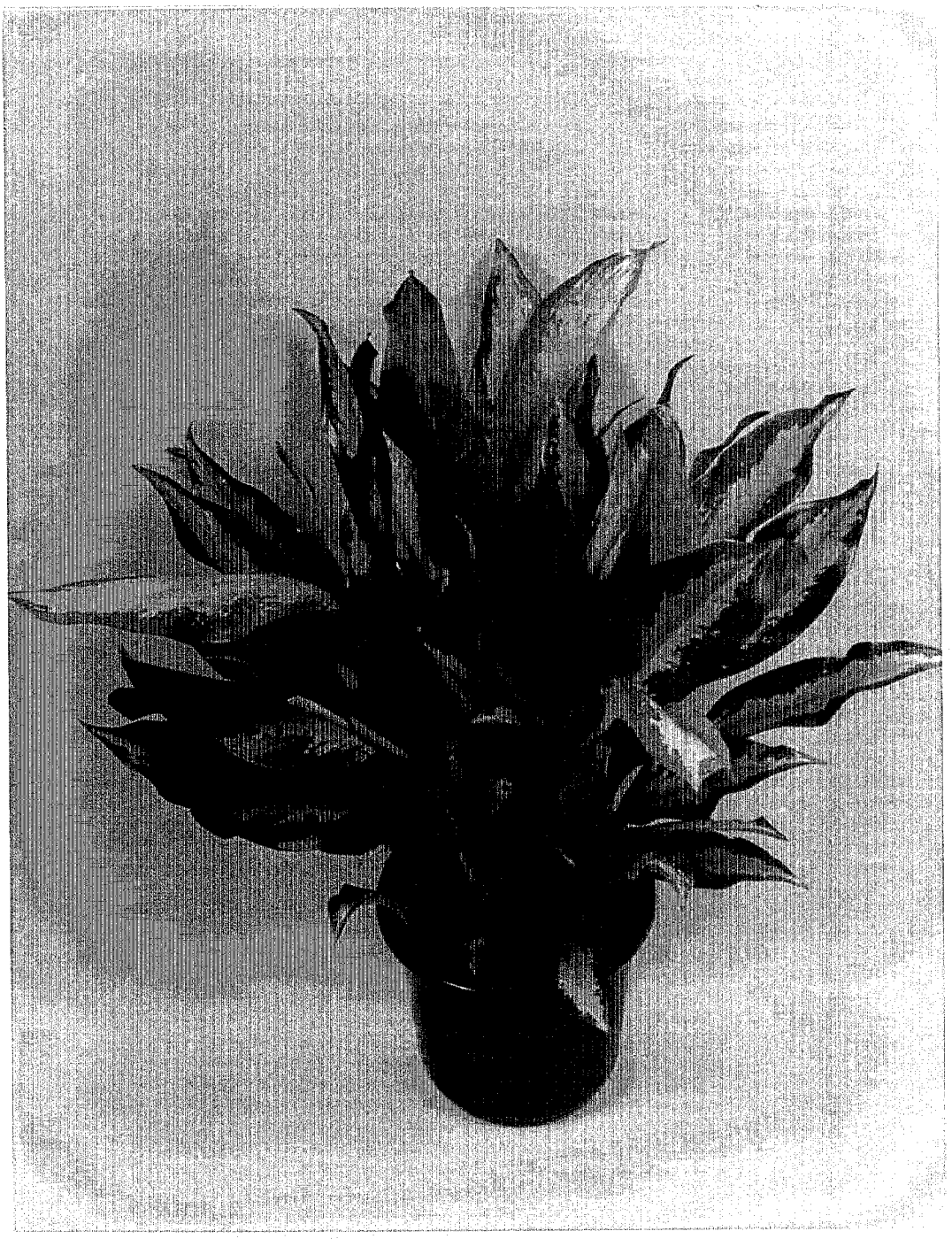

* * * * *